(12) United States Patent
Krishnamachari et al.

(10) Patent No.: US 10,132,754 B2
(45) Date of Patent: Nov. 20, 2018

(54) DEVICE AND METHOD FOR ILLUMINATING A SAMPLE

(71) Applicant: LEICA MICROSYSTEMS CMS GMBH, Wetzlar (DE)

(72) Inventors: Vishnu Vardhan Krishnamachari, Seeheim-Jugenheim (DE); Volker Seyfried, Nussloch (DE); William C. Hay, Heppenheim (DE); Manuel Kremer, Leimen (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 185 days.

(21) Appl. No.: 15/037,451

(22) PCT Filed: Nov. 19, 2014

(86) PCT No.: PCT/EP2014/075055
§ 371 (c)(1),
(2) Date: May 18, 2016

(87) PCT Pub. No.: WO2015/075089
PCT Pub. Date: May 28, 2015

(65) Prior Publication Data
US 2016/0290928 A1 Oct. 6, 2016

(30) Foreign Application Priority Data
Nov. 19, 2013 (DE) .................. 10 2013 112 750

(51) Int. Cl.
*G01N 21/00* (2006.01)
*G01N 21/65* (2006.01)
(Continued)

(52) U.S. Cl.
CPC ......... *G01N 21/65* (2013.01); *G02B 21/0032* (2013.01); *G02B 21/0076* (2013.01);
(Continued)

(58) Field of Classification Search
CPC ............ G01N 21/65; G01N 2021/653; G01N 2021/06113; G02B 21/0032; G02B 21/0076; G02B 21/16
See application file for complete search history.

(56) References Cited

U.S. PATENT DOCUMENTS

2006/0192969 A1 8/2006 Marks et al.

OTHER PUBLICATIONS

International Searching Authority, Written Opinion of the International Searching Authority for PCT/EP2014/075055 dated May 28, 2015.
(Continued)

*Primary Examiner* — Armando Rodriguez
(74) *Attorney, Agent, or Firm* — Hodgson Russ LLP

(57) ABSTRACT

A device (10) for illuminating a sample (40) is described, having: at least one pulsed laser light source (12) for repeated emission of a first laser pulse along a first light path (14) and of a second laser pulse along a second light path (16) physically separated from the first light path; a superimposition element (32) for collinear superimposition of the two laser pulses in a shared light path (34); a delay stage (26) arranged in the first or the second light path (14, 16), for delaying one of the two laser pulses relative to the other laser pulse in such a way that the two laser pulses sent along the shared light path (34) onto the sample (40) exhibit a temporal superimposition; a shared chirp unit (36) arranged in the shared light path (34), for frequency-modifying influencing both of the first laser pulse and of the second laser pulse; and at least one separate chirp unit (18) arranged in the first light path (14), for frequency-modifying influencing only of the first laser pulse. The shared chirp unit (36) and the separate chirp unit (18) are coordinated with one another in order to achieve a target state. The separate chirp unit (18) is coupled to a control system (20) by which the separate
(Continued)

chirp unit (18) is controllable with a control parameter dependent on the wavelength of the first laser pulse in order to establish the target state.

15 Claims, 10 Drawing Sheets

(51) Int. Cl.
    *G02B 21/00*     (2006.01)
    *G02B 21/16*     (2006.01)

(52) U.S. Cl.
    CPC ....... *G02B 21/16* (2013.01); *G01N 2021/653* (2013.01); *G01N 2201/06113* (2013.01)

(56) References Cited

OTHER PUBLICATIONS

Rocha-Mendoza, et al., Coherent anti-Stokes Raman microspectroscopy using spectral focusing with glass dispersion, Applied Physics Letters, vol. 93, p. 201103, pp. 1-3 Nov. 18, 2008.

Rocha-Mendoza, et al., Differential coherent anti-Stokes Raman scattering microscopy with linearly chirped femtosecond laser pulses, Optics Letters, vol. 34, No. 15, pp. 2258-2260 Aug. 1, 2009.

Nandakumar, et al., Vibrational imaging based on stimulated Raman scattering microscopy, New Journal of Physics, vol. 11, p. 033026, pp. 1-9 Mar. 25, 2009.

Freudiger, et al., Optical Heterodyne-Detected Raman-Induced Kerr Effect (OHD-RIKE) Microscopy, The Journal of Physical Chemistry B, vol. 115, pp. 5574-5581 Apr. 19, 2011.

Slipchenko, et al., Heterodyne detected nonlinear optical imaging in a lock-in free manner, Journal of Biophotonics, vol. 5, No. 10, pp. 801-807 Mar. 5, 2012.

Zumbush, et al., Three-Dimensional Vibrational Imaging by Coherent Anti-Stokes Raman Scattering, Physical Review Letters, vol. 82, No. 20, pp. 4142-4145 May 17, 1999.

Cheng, et al., Coherent Anti-Stokes Raman Scattering Microscopy: Instrumentation, Theory, and Applications, Journal of Physical Chemistry B, vol. 108, pp. 827-840 Dec. 25, 2003.

Evans, et al., Coherent Anti-Stokes Raman Scattering Microscopy: Chemical Imaging for Biology and Medicine, Annual Review of Analytical Chemistry, vol. 1, pp. 883-909 Jul. 1, 2008.

Dujdovich, et al., Single-pulse coherently controlled nonlinear Raman spectroscopy and microscopy, Nature, vol. 418, pp. 512-514 Aug. 1, 2002.

Hellerer, et al., Spectral focusing: High spectral resolution spectroscopy with broad-bandwidth laser pulses, Applied Physics Letters, vol. 85, No. 1, pp. 25-27 Jul. 5, 2004.

Pegoraro, et al., Optimally chirped multimodal CARS microscopy based on a single Ti:sapphire oscillator, Optics Express, vol. 17, No. 4, pp. 2984-2996 Feb. 16, 2009.

Saar, et al., Video-Rate Molecular Imaging in Vivo with Stimulated Raman Scattering, Science, vol. 330, No. 6009, pp. 1368-1370 Dec. 3, 2010.

FIG. 11

DEVICE AND METHOD FOR ILLUMINATING A SAMPLE

CROSS-REFERENCE TO RELATED APPLICATIONS

The present application is the U.S. national phase of International Application No. PCT/EP2014/075055 filed Nov. 19, 2014, which claims priority of German Application No. 10 2013 112 750.9 filed Nov. 19, 2013, the entirety of which is incorporated herein by reference.

FIELD OF THE INVENTION

The invention relates to a device for illuminating a sample, having: at least one pulsed laser light source for repeated emission of a first laser pulse along a first light path and of a second laser pulse along a second light path physically separated from the first light path; a superimposition element for collinear superimposition of the two laser pulses in a shared light path; a delay stage, arranged in the first or the second light path, for delaying one of the two laser pulses relative to the other laser pulse in such a way that the two laser pulses sent along the shared light path onto the sample exhibit a temporal superimposition; a shared chirp unit, arranged in the shared light path, for frequency-modifying influencing both of the first laser pulse and of the second laser pulse; and at least one separate chirp unit, arranged in the first light path, for frequency-modifying influencing only of the first laser pulse, the shared chirp unit and the separate chirp unit being coordinated with one another in order to achieve a target state in which an instantaneous frequency of the first laser pulse influenced both by the separate chirp unit and by the shared chirp unit, and an instantaneous frequency of the second laser pulse influenced only by the shared chirp unit, have a predetermined relationship to one another. The invention further relates to a corresponding method for illuminating a sample.

BACKGROUND OF THE INVENTION

Coherent Raman scattering microscopy (abbreviated "CRSM") has recently acquired considerable significance in image-producing chemical sample analysis, for example in biology, pharmacy, or food science. A variety of CRSM methods are utilized, for example coherent anti-Stokes Raman scattering (CARS), coherent Stokes-Raman scattering (CSRS), Raman-induced Kerr effect scattering (RIKES), and stimulated Raman scattering (SRS). The list of documents below will be referred to hereinafter regarding the existing art:

[1] Nandakumar, P., Kovalev, A., Volkmer, A.: "Vibrational imaging based on stimulated Raman scattering microscopy," New Journal of Physics, 2009, 11, 033026.
[2] Freudiger, C. W., Roeffaers, M. B. J., Zhang, X., Saar, B. G., Min, W., Xie, X. S.: "Optical heterodyne-detected Raman-induced Kerr effect (OHD-RIKE) microscopy," Journal of Physical Chemistry B, 2011, 115, 5574-5581.
[3] Saar, B. G., Freudiger, C. W., Reichman, J., Stanley, C. M., Holtom, G. R., Vie, X. S.: "Video-rate molecular imaging in vivo with stimulated Raman scattering," Science, 2010, 330, 1368-1370.
[4] Mikhail N. Slipchenko, Robert A. Oglesbee, Delong Zhang, Wei Wu, Ji-Xin Cheng: "Heterodyne detected nonlinear optical imaging in a lock-in free manner," J. Biophotonics, 2012, 5, 1-7.
[5] Zumbusch, A., Holtom, G. R., Xie, X. S.: "Three-dimensional vibrational imaging by coherent anti-Stokes Raman scattering," Phys. Rev. Lett., 1999, 82, 4142-4145.
[6] Cheng, J. X. and Xie, X. S.: "Coherent anti-Stokes Raman scattering microscopy: Instrumentation, theory, and applications," J. Phys. Chem. B, 2004, 108, 827-840.
[7] Evans, C. L. and Xie, X. S.: "Coherent anti-Stokes Raman scattering microscopy: chemical imaging for biology and medicine," Annu. Rev. Anal. Chem., 2008, 1, 883-909.
[8] Dudovich, N., Oron, D., Silberberg, Y.: "Single-pulse coherently controlled nonlinear Raman spectroscopy and microscopy," Nature, 2002, 418, 512-514.
[9] Hellerer, T., Enejder, A. M. K., Zumbusch, A.: "Spectral focusing: High spectral resolution spectroscopy with broad-bandwidth laser pulses," Applied Physics Letters, 2004, 85, 25-27.
[10] Israel Rocha-Mendoza, Wolfgang Langbein, Paola Borri: "Coherent anti-Stokes Raman microspectroscopy using spectral focusing with glass dispersion," Applied Physics Letters, 2008, 93, 201103:1-201103:3.
[11] Adrian F. Pegoraro, Andrew Ridsdale, Douglas J. Moffatt, Yiwei Jia, John Paul Pezacki, Albert Stolow: "Optimally chirped multimodal CARS microscopy based on a single Ti:sapphire oscillator," Optics Express, 2009, 17, 2984-2996.

In the CRSM technique, two pulsed light fields having pulse widths in a range from 100 fs to 20 ps, of different wavelengths, are directed through a confocal microscope optical system and focused onto the sample. The pulsed light fields, having frequencies that are typically in a range from 1 to 100 MHz, are emitted from a short-pulse laser light source. The light fields are spatially and temporally superimposed on one another on the sample via corresponding beam guidance and suitable focusing optics. "Temporal superimposition" is to be understood as pair-wise coincidence of the laser pulses forming the pulsed light fields. In the SRS method or the image-producing superimposed RIKES method, for example, one of the two light fields is modulated in terms of intensity, frequency, or polarization at a specific frequency that is typically in the kHz to MHz range, before interacting in the sample with the other light field. For SRS and RIKES image production, the initially unmodulated light field is then sensed and, using a lock-in technique or envelope curve demodulation technique, the intensity modulation is extracted and presented in the form of an image. Reference is made to documents [1], [2], and [3] regarding implementation of the lock-in technique. The envelope curve demodulation technique is described in document [4]. In the case of CARS and CSRS a third light field is sensed as a result of interaction with the sample and displayed as an image. This is described in documents [5], [6], and [7].

In all the CRSM techniques recited above, the measured signal is only strong if the difference between the frequencies of the incident light fields coincides with a vibrational resonance frequency in the sample. At present, the best images in terms of spectral selectivity, signal intensity, and signal to noise ratio are obtained using picosecond laser light sources and optical parametric oscillators (OPOs) having pulse widths from 5 to 7 ps.

Femtosecond lasers are also widely used nowadays, however, for example in multi-photon fluorescence microscopy and in microscopy techniques based on the principle of frequency doubling (SHG) or frequency tripling (THG). Considerable effort is therefore being devoted to using femtosecond lasers in CRSM imaging as well. Reference is made in this regard, for example, to documents [8], [9], [10], and [11].

The use of a femtosecond laser or of an optical parametric oscillator for CRSM has the considerable disadvantage, however, of poor spectral selectivity. This will be explained below with reference to FIGS. 1 and 2, in which the CARS emission achieved by excitation with a picosecond laser (FIG. 1) is compared, by way of example, with the CARS emission achieved by excitation with a femtosecond laser.

FIG. 1 shows, purely schematically, a term diagram of a sample that has a vibrational ground state |g> and a state system |v|> having a set of first excited vibrational states a, b, c. These first excited vibrational states a, b, c have energy levels that are attributable to three different molecular bonds, e.g. N—H, O—H, and C—H. In the CARS method two laser beams, one of which is referred to as a "pump beam" and the other as a "Stokes beam," are directed onto the sample. The energy difference between these beams coincides with the energy of one of the vibrational states. A probe beam, which probes the vibrational coherence, is also used.

In the case shown in FIG. 1, in which CARS emission is excited with a picosecond laser, the pump beam and the Stokes beam are spectrally comparatively narrow-band. This is due to the circumstance, known from Fourier analysis, that as the extent of a laser pulse over time increases, the spectral distribution of the frequencies contained in the laser pulse becomes narrower. It is accordingly possible to selectively excite the vibrational states a, b, c using the picosecond laser.

FIG. 2, in contrast, illustrates the corresponding situation when a femtosecond laser is used instead of the picosecond laser. Because the time-related pulse widths of the pump beam and Stokes beam are smaller in this case, the spectral widths of the laser pulses correspondingly increase. It is consequently no longer possible to selectively excite the individual vibrational states a, b, c. Spectral selectivity is thus negatively affected by the spectrally broad-band excitation of the femtosecond laser.

A variety of methods, known in the literature under the keywords "spectral focusing," have been proposed as a solution to this problem. Reference is made in this regard to document [10]. In this, two glass blocks of predetermined length are used, one of which is arranged in the light path of the Stokes beam while the other is located in a shared light path into which the Stokes beam and pump beam are combined. Each of these two glass blocks brings about, as a result of dispersion, a spectral broadening of the laser pulse passing through it. The glass blocks thus form so-called "chirp" units. The term "chirp" is to be understood here as a frequency-modifying influencing of the laser light, which can bring about e.g. a time-related stretching of the respective laser pulse but also a time-related compression of the laser pulse.

In the arrangement known from document [10], the dispersive effects of the two glass blocks as a function of the wavelengths of the pump beam and of the Stokes beam are selected so that the pertinent laser pulses, superimposed on one another on the sample, are coordinated with one another in the desired fashion, spectrally and in terms of time, in order to achieve the desired spectral focusing. For this, the glass blocks used as chirp units must be configured exactly for the wavelengths of the pump beam and Stokes beam. If other wavelengths are to be used, the glass blocks must be replaced with correspondingly modified units. This is costly and involves considerable complexity for the user.

SUMMARY OF THE INVENTION

The object on which the invention is based is that of describing a device and a method for illuminating a sample which enable flexibly manageable and user-friendly illumination of the sample.

The invention achieves this object by way of the subject matter of the independent claims. Advantageous refinements of the invention are described in the dependent claims.

The invention firstly provides adjustability, in a predetermined wavelength range, at least of the wavelength of the first light pulse emitted along the first light path. In order to enable the desired spectral focusing independently of the wavelength currently set, the separate chirp unit acting in the first light path on the first light pulse is furthermore embodied as a unit controllable as a function of the wavelength currently set. A control system coupled to the separate chirp unit is accordingly provided, which system controls the chirp unit with a control parameter dependent on the wavelength of the first laser pulse in order to establish a desired target state, in particular spectral focusing. The illumination device according to the present invention can thus be used flexibly over a wide wavelength range with no need to modify or replace the chirp units provided for achieving spectral focusing. This considerably simplifies handling of the device.

The invention is configured in particular for the use of a femtosecond laser as a pulsed laser light source, but is not limited thereto. It is thus also conceivable to use, for example, a picosecond laser as a pulsed laser light source.

Preferably, in the target state the difference between the instantaneous frequency of the first laser pulse influenced both by the separate chirp unit and by the shared chirp unit, and the instantaneous frequency of the second laser pulse influenced only by the shared chirp unit, is constant during the temporal superimposition of the two laser pulses. The fact that the separate chirp unit is controlled in such a way that the aforementioned difference between the instantaneous frequencies of the two laser pulses at the sample is constant over time ensures that, for example in a CRSM application, the same frequency difference is established, and thus the device according to the present invention remains spectrally focused, for the time during which the two laser pulses are temporally superimposed on one another. It is moreover possible to variably adjust the difference between the instantaneous frequencies of the two laser pulses at the sample, for example in order to selectively excite different vibrational states in a CRSM method, simply by delaying one of the two laser pulses relative to the other laser pulse.

The shared chirp unit, for example, expands the first laser pulse and the second laser pulse that propagate along the second light path. For this, the shared chirp unit acts on the two laser pulses in such a way that laser pulse components of shorter wavelength are delayed with respect to laser light components of longer wavelength. This type of frequency-modifying influencing is also referred to as a "positive chirp." A "negative chirp," conversely, exists when the laser pulse components of longer wavelength are delayed with respect to the laser pulse components of shorter wavelength.

If the invention is applied, for example, to a CRSM method, working with a pump beam of variable wavelength and a Stokes beam of fixed wavelength, such that the fixed wavelength is longer than the variable wavelength of the pump beam, the separate chirp unit acting on the pump beam can then be controlled in such a way that it impinges upon the pump beam with a negative chirp in order to maintain a constant difference between the instantaneous frequencies of the two laser pulses at the sample.

The shared chirp unit that acts on both the first and the second laser pulse is embodied, for example, as a glass block. Conversely, the separate chirp unit controllable according to the present invention is constituted, for example, by optical elements, e.g. mirrors and/or gratings, that can be moved with respect to one another as a function of the wavelength-dependent control parameter in order to achieve the desired frequency-modifying influencing of the first laser pulse.

The shared chirp unit acting both on the first and on the second laser pulse can also be constituted by an optical modulator or an optical filter that is required in any case in the device according to the present invention, for example for intensity modulation or wavelength filtering, provided the chirp brought about by that element is sufficiently large that an additional (shared) chirp element can be dispensed with.

It is furthermore possible to provide an additional separate chirp unit that is arranged in the second light path for frequency-modifying influencing only of the second laser pulse. In this case both the first and the second chirp unit are controlled in the manner according to the present invention in order to ensure selective focusing of the two light pulses at the sample in the entire wavelength range within which the wavelength of one or both light pulses is varied.

In a preferred embodiment the at least one controllable chirp unit is contained in the pulsed laser light source. This embodiment exploits the fact that conventional pulsed laser light sources often possess a so-called pre-chirp unit that is now used according to the present invention to ensure spectral focusing over the entire wavelength range within which the wavelength of one or both laser pulses is varied. The invention thus provides for a pre-chirp unit of this kind, incorporated into the pulsed laser light source, to be controlled in a manner that appreciably differs from conventional control application. For example, in the existing art pre-chirp units are generally set so that the pulse duration of the light pulses emitted from the short-pulse laser light source is as short as possible at the sample. In a departure from this conventional control application, on the other hand, the aim of control application according to the present invention to the pre-chirp unit integrated into the short-pulse laser light source is spectral focusing, which is not necessarily accompanied by the shortest possible pulse widths.

Instead of an integrated pre-chirp unit it is also possible to use an external controllable chirp unit, i.e. a chirp unit that is arranged outside the pulsed laser light source.

The first laser pulse and the second laser pulse can respectively be approximated by a Gaussian pulse whose normalized electric field $E(z,T)$ is described by the following equation:

$$E(z, T) = \exp\left(-\frac{(1 + iC)T^2}{2T_o^2}\right)\exp^{-i(kz-\omega T)},$$

the control parameter being defined in such a way that the variable $$\frac{C}{T_0^2}$$

is identical for the first laser pulse and the second laser pulse. Assuming, for example, that in a CRSM method the first laser pulse of variable wavelength is provided by a pump beam and the second laser pulse of fixed wavelength is provided by a Stokes beam, the best possible spectral focusing is then obtained when the variable $$\frac{C}{T_0^2}$$

is identical for both beams. Once the short-pulse laser light source and the separate chirp unit acting on the pump beam have been characterized, the delay between the two beams, the chirp parameter C, and the respective pulse width $T_0$ as a function of the variably adjustable wavelength, as well as possible values of the control parameter with which the separate chirp unit is controlled, are known. Based on this information it is possible to keep on hand calibration data, for example in the form of a multidimensional calibration table that the control system accesses in order to determine the control parameter as well as the correct delay between the two laser pulses, which make possible optimum spectral focusing.

The concept explained above for achieving optimum spectral focusing relates to an embodiment in which a controllable chirp unit is provided only in one of the two light paths. This concept is also applicable, however, to embodiments in which a respective controllable chirp unit is located in each of the two light paths. In this case as well, the control parameter can be determined according to the present invention for each of the two controllable chirp units in such a way that the desired spectral focusing is achieved.

Preferably a calibration is carried out in order to ascertain calibration data, on the basis of which the control parameter is determined by means of the control system. In the context of calibration, preferably a chirp parameter is ascertained, as an indicator of the chirp impingement upon the respective laser pulse by the shared chirp unit, both for the first laser pulse and for the second laser pulse.

The calibration makes provision, for example, for determining at least the chirp parameter relating to the first laser pulse by: measuring the pulse duration of the first laser pulse for predefined values of the control parameter and for predefined values of the wavelength of the first laser pulse, both in the first light path after passing through the separate chirp unit and in the shared light path after passing through the shared chirp unit; ascertaining therefrom a pulse duration difference; and calculating the chirp parameter on the basis of that pulse duration difference. For the case in which the second laser pulse is also influenced in frequency-modifying fashion by a controllable chirp unit, a corresponding calibration is accomplished in order to determine a chirp parameter related to the second laser pulse.

If the difference between the instantaneous frequency of the first laser pulse and the instantaneous frequency of the second laser pulse, which is constant during the temporal superimposition of the two laser pulses, is to be modified, for example in a CRSM method in order to coordinate that frequency difference with a vibration state that is to be excited, then the delay stage, which delays one of the two laser pulses relative to the other laser pulse, is controlled with a wavelength-dependent delay parameter. Outstanding spectral selectivity of the method according to the present invention can be achieved with the aid of this wavelength-dependent delay parameter.

The delay parameter is preferably ascertained on the basis of further calibration data that are determined by ascertaining the delay of one of the two laser pulses relative to the other laser pulse for predefined values of the control parameter and predefined values of the wavelength of the first laser pulse. These further calibration data can be stored, for example, in the form of a calibration table that the control system accesses as necessary.

BRIEF DESCRIPTION OF THE DRAWING VIEWS

The invention will be explained below in further detail with reference to the Figures, in which:

FIG. 11 shows a first calibration table for determining the control parameter, and a second calibration table for determining the delay parameter.

DETAILED DESCRIPTION OF THE INVENTION

Figure 2:
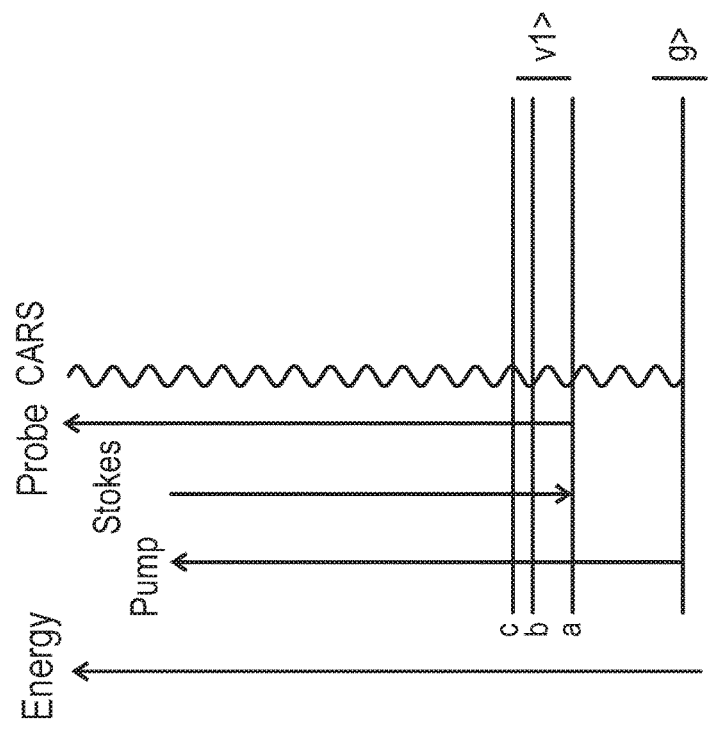
FIG. 2 is a term diagram to illustrate a CARS emission upon excitation with a femtosecond laser.
Figure 1:
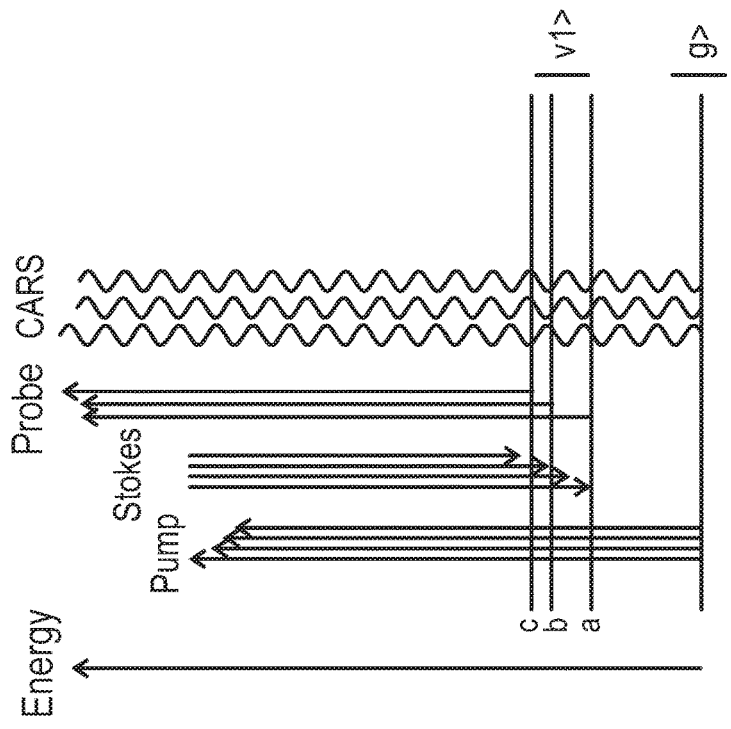
FIG. 1 is a term diagram to illustrate a CARS emission upon excitation with a picosecond laser.
Figure 3:
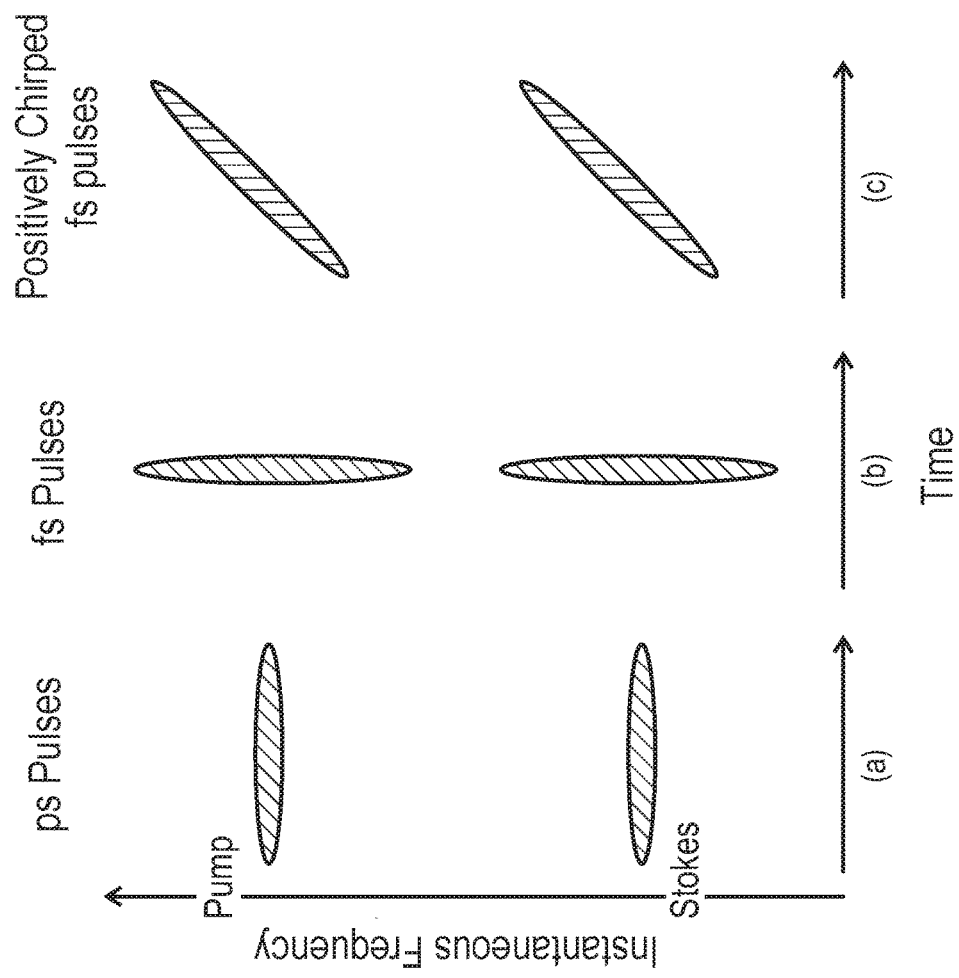
FIG. 3 is a schematic depiction to explain spectral focusing according to the present invention.

The concept of spectral focusing according to the present invention will first be explained with reference to what is depicted in FIG. 3.

FIG. 3 shows in sub-Figures (a), (b), and (c), both for a Stokes laser pulse and for a pump laser pulse, the respective instantaneous frequency as a function of time. Sub-Figure (a) depicts a situation in which the Stokes laser pulse and the pump laser pulse are outputted by a picosecond laser. Sub-Figure (b) shows a situation in which the Stokes laser pulse and the pump laser pulse are emitted by a femtosecond laser with no chirp impingement upon the two laser pulses. Lastly, sub-Figure (c) illustrates a situation in which the Stokes laser pulse and the pump laser pulse are again sent out by a femtosecond laser, but are now also impinged upon by a positive chirp.

As sub-Figure (a) of FIG. 3 shows, the laser pulses outputted by the picosecond laser have a comparatively large time-related pulse width. The spectral width of the respective laser pulse over which the instantaneous frequency varies is correspondingly comparatively small. The difference between the instantaneous frequency of the pump laser pulse and the instantaneous frequency of the Stokes laser pulse is thus largely constant over the time during which the two laser pulses are superimposed on one another. Good spectral focusing thus exists.

As sub-Figure (b) of FIG. 3 shows, the laser pulses sent out by the femtosecond laser have a smaller time-related pulse width and accordingly a greater spectral width. A number of combinations thus exist, during the temporal superimposition of the two laser pulses, between possible instantaneous frequencies of the pump laser pulse and possible instantaneous frequencies of the Stokes laser pulse. The result of this plurality of possible frequency combinations is appreciably poorer spectral focusing.

In the situation shown in sub-Figure (c) of FIG. 3, this degradation in spectral focusing caused by the use of the femtosecond laser is eliminated by impinging upon the two laser pulses with a positive chirp. The positive chirp thus provides a stretching over time of the time-related pulse widths, in such a way that the difference between the instantaneous frequency of the pump laser pulse and the instantaneous frequency of the Stokes laser pulse during the temporal superimposition of the two laser pulses is once again largely constant.

Figure 4:
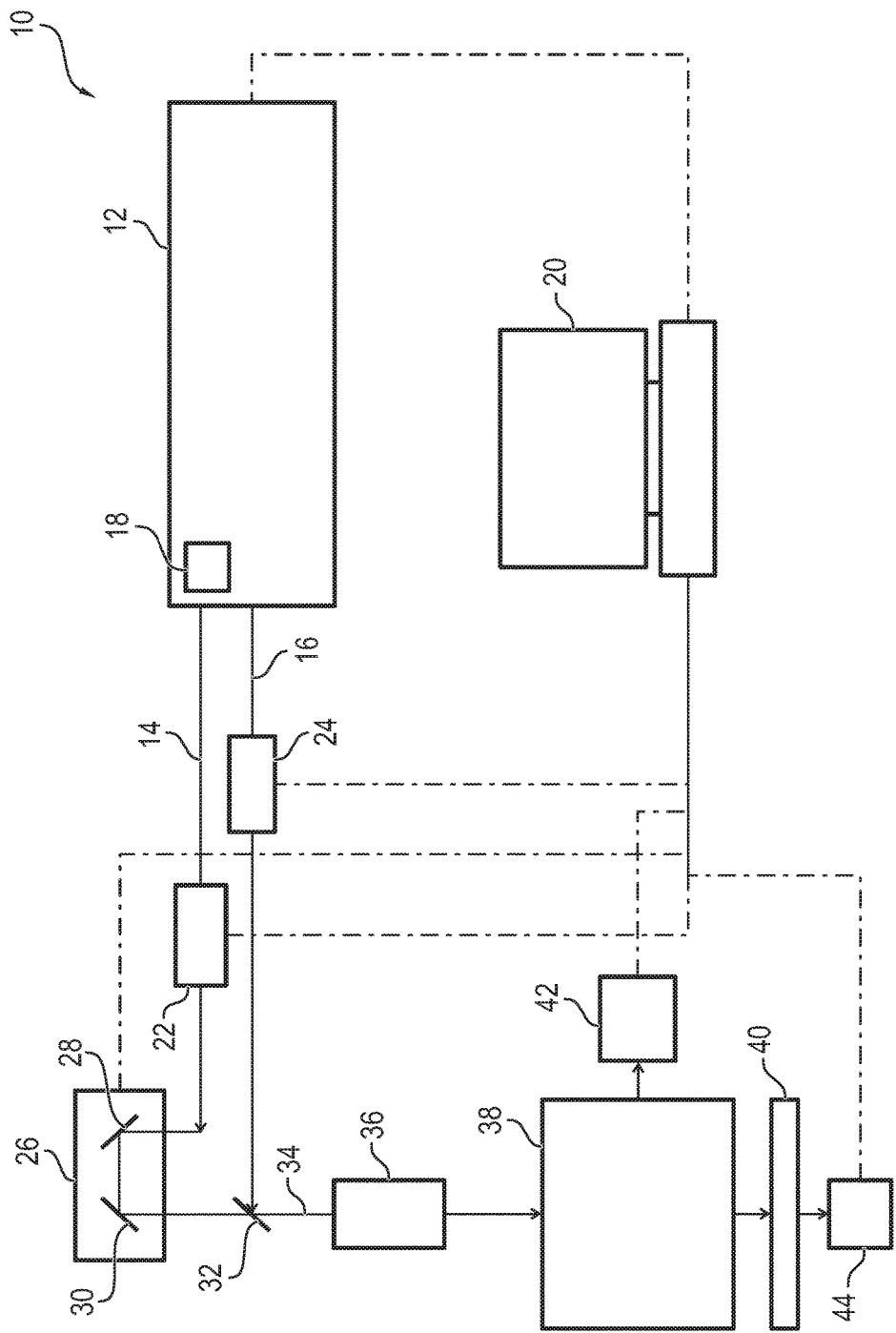
FIG. 4 shows an exemplifying embodiment of the device according to the present invention.

FIG. 4 schematically depicts a device 10 as an embodiment according to the present invention.

Device 10 contains a pulsed laser light source in the form of a femtosecond laser 12. Femtosecond laser 12 has two outputs through which it emits a first laser pulse signal along a first light path 14 and a second laser pulse signal along a second light path 16. In the present embodiment femtosecond laser 12 is embodied in such a way that the wavelength of the first laser pulse signal, constituted by a sequence of first laser pulses, can be adjusted in a predetermined wavelength range. The second laser pulse signal, however, constituted by a sequence of second laser pulses, is emitted from femtosecond laser 12 at a fixed wavelength.

Femtosecond laser 12 contains an integrated chirp unit 18 that is constituted, for example, by optical elements movable with respect to each other, such as mirrors or gratings. The integrated chirp unit 18 is controlled via a control system 20, e.g. a computer coupled to femtosecond laser 12. This control application is effected via a control parameter according to which the optical elements constituting chirp unit 18 are moved with respect to one another in order to influence the respective first laser pulse in frequency-modifying fashion in the desired manner, i.e. to impinge upon it with the desired chirp.

The first laser pulse emitted from femtosecond laser 12 passes, in first light path 14, through an optical element 22 coupled to control system 20, which element modulates or regulates the light intensity. Optical element 22 is, for example, an electro-optical or acousto-optical modulator (abbreviated EOM or AOM, respectively), or a combination of a half-wave plate and a polarizing beam splitter. The second laser pulse correspondingly passes, along second light path 16, through a correspondingly embodied second optical element 24.

Arranged in first light path 14 is an optical delay stage 26 that is constituted by two mirrors 28 and 30 movable with respect to each other. Delay stage 30 is likewise connected to control system 20. The distance between the two mirrors 28 and 30 can be adjusted by way of control system 20 as a function of a delay parameter, in order to delay the first laser pulse relative to the second laser pulse in such a way that a temporal superimposition is brought about between these two laser pulses.

The first laser pulse emerging from delay stage 26, and the second laser pulse, strike a dichroic or polarizing beam splitter 32 that combines first light path 14 and second light path 16 collinearly into one shared light path 34. The two laser pulses, superimposed on one another, are then directed along shared light path 34 through a glass block 36 that stretches the two laser pulses over time. The two laser pulses are then directed through an optical system 38, which for example encompasses a confocal microscope optical system, onto a sample 40.

A measured signal generated by interaction of the first and second laser pulse with sample 40 can be captured by means of an epi-detector 42 and/or a forward detector 44. The two detectors 42 and 44 are coupled to control system 20 for purposes of control application and evaluation.

Glass block 36 influences both the first laser pulse and the second laser pulse in such a way that the two laser pulses are impinged upon by a positive chirp in order to stretch the pulse over time. Chirp unit 18, contained in femtosecond laser 12 and controllable by control system 20, has the function of influencing the laser pulse in frequency-modifying fashion in such a way that the two laser pulses are focused at sample 40 in the manner illustrated in sub-Figure (c) of FIG. 3. If it is assumed, for example, that the variable wavelength of the first laser pulse emitted from femtosecond laser 12 is shorter than the fixed wavelength of the second laser pulse, then chirp unit 18 integrated into femtosecond laser 12 impinges upon the first laser pulse with a negative chirp.

The control parameter with which control system 20 controls chirp unit 18 integrated into femtosecond laser 12 for frequency-modifying influencing of the first laser pulse is determined, in a manner explained later, as a function of the wavelength of the first laser pulse.

Embodiments that are modified with respect to the embodiment shown in FIG. 4 will be described below with reference to FIGS. 5 to 9. In these modified embodiments, the components which correspond to those of the embodiment according to FIG. 4 are labeled with the reference characters used in FIG. 4.

Figure 5:
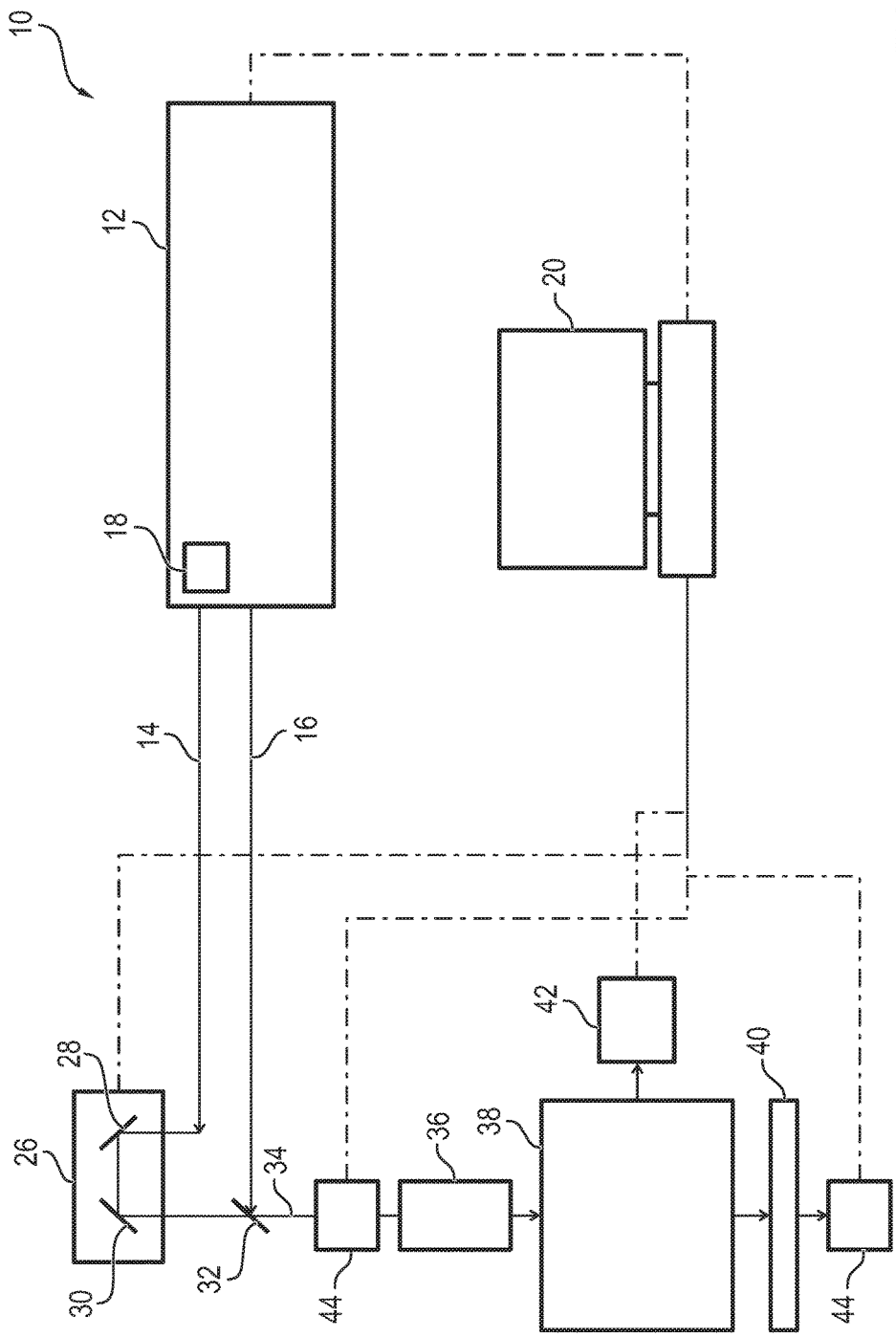
FIG. 5 shows a modified embodiment of the device according to the present invention.

The modified embodiment according to FIG. 5 differs from the device according to FIG. 4 in that instead of optical elements 22, 24 that are arranged respectively in the separate light paths 14, 16, an element 44 arranged in shared light path 34 is provided. Optical element 44, which acts both on the first laser pulse and on the second laser pulse, is e.g. an AOM or EOM. It can also be embodied as an optical filter, for example as an acousto-optical tunable filter (abbreviated AOTF).

Figure 6:
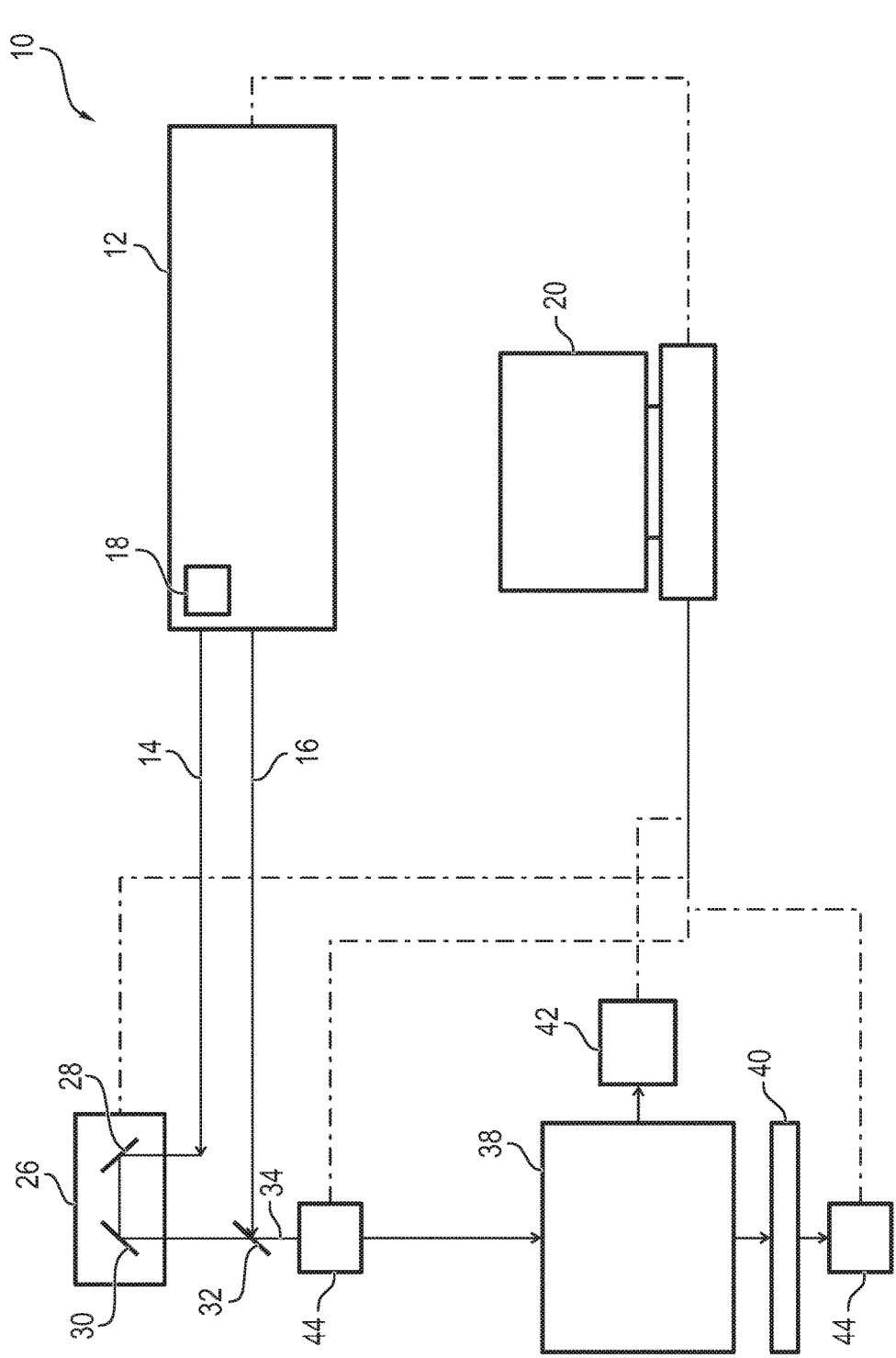
FIG. 6 shows a further modified embodiment of the device according to the present invention.

The embodiment shown in FIG. 6 differs from the embodiment according to FIG. 5 in that glass block 36 impinging with a positive chirp upon the two laser pulses in the shared light path is omitted. In this embodiment only optical element 44, i.e. the AOM, EOM, or AOTF, functions as a shared chirp element acting on both laser pulses. The chirp brought about by optical element 44, i.e. the frequency-modifying influencing of the two laser pulses, is consequently sufficiently large that no further chirp unit in the form of a glass block is required.

Figure 7:
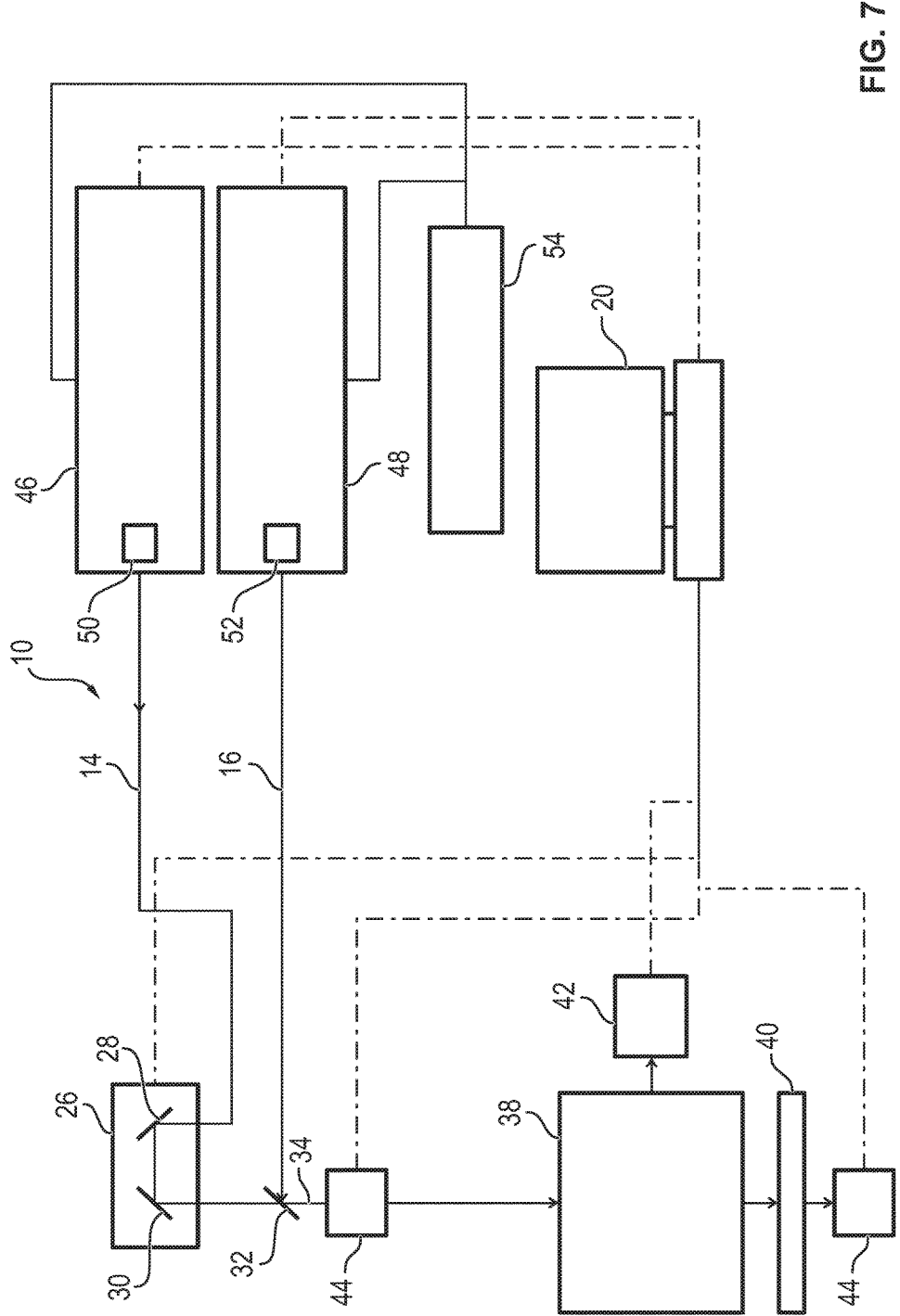
FIG. 7 shows a further modified embodiment of the device according to the present invention.

In the embodiment according to FIG. 7, instead of the single femtosecond laser 12 two separate femtosecond lasers 46 and 48 are provided, which respectively contain an integrated chirp unit 50 and 52. The pulse repetition rates at which the two femtosecond lasers 46, 48 respectively emit the first and the second laser pulse are controlled via a laser synchronization unit 54.

In the embodiment according to FIG. 7 the two integrated chirp units 50, 52 are again controlled via control system 20 in such a way that optimum spectral focusing in accordance with sub-Figure (c) of FIG. 3 is achieved.

Figure 8:
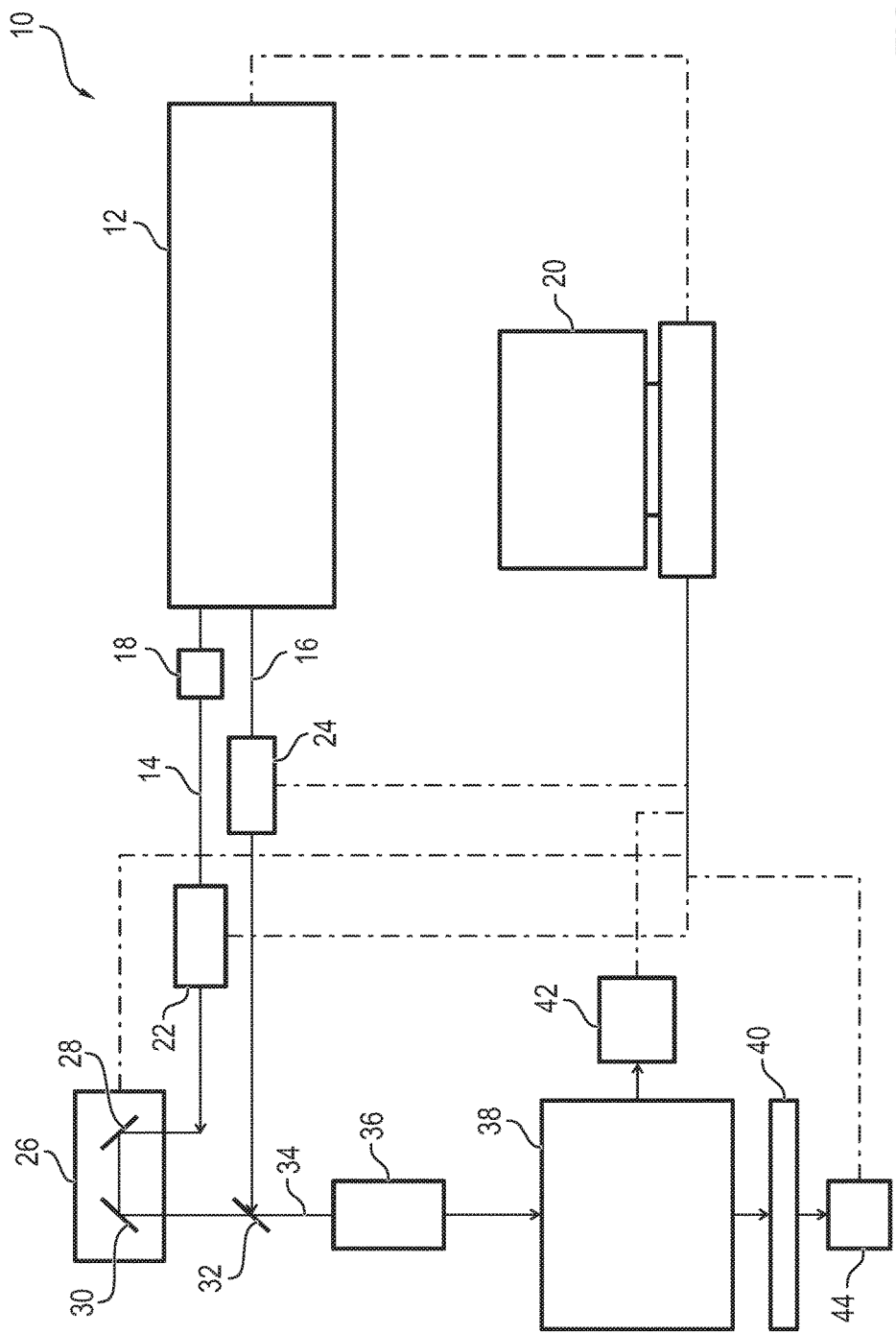
FIG. 8 shows a further modified embodiment of the device according to the present invention.

The embodiment according to FIG. 8 differs from the embodiment depicted in FIG. 4 in that chirp unit 18 associated with first light path 14 is not contained in femtosecond laser 12 as a pre-chirp unit but instead is arranged as an external unit outside femtosecond laser 12. External chirp unit 18 is controlled by control system 20 in the same way as in the embodiment according to FIG. 4.

Figure 9:
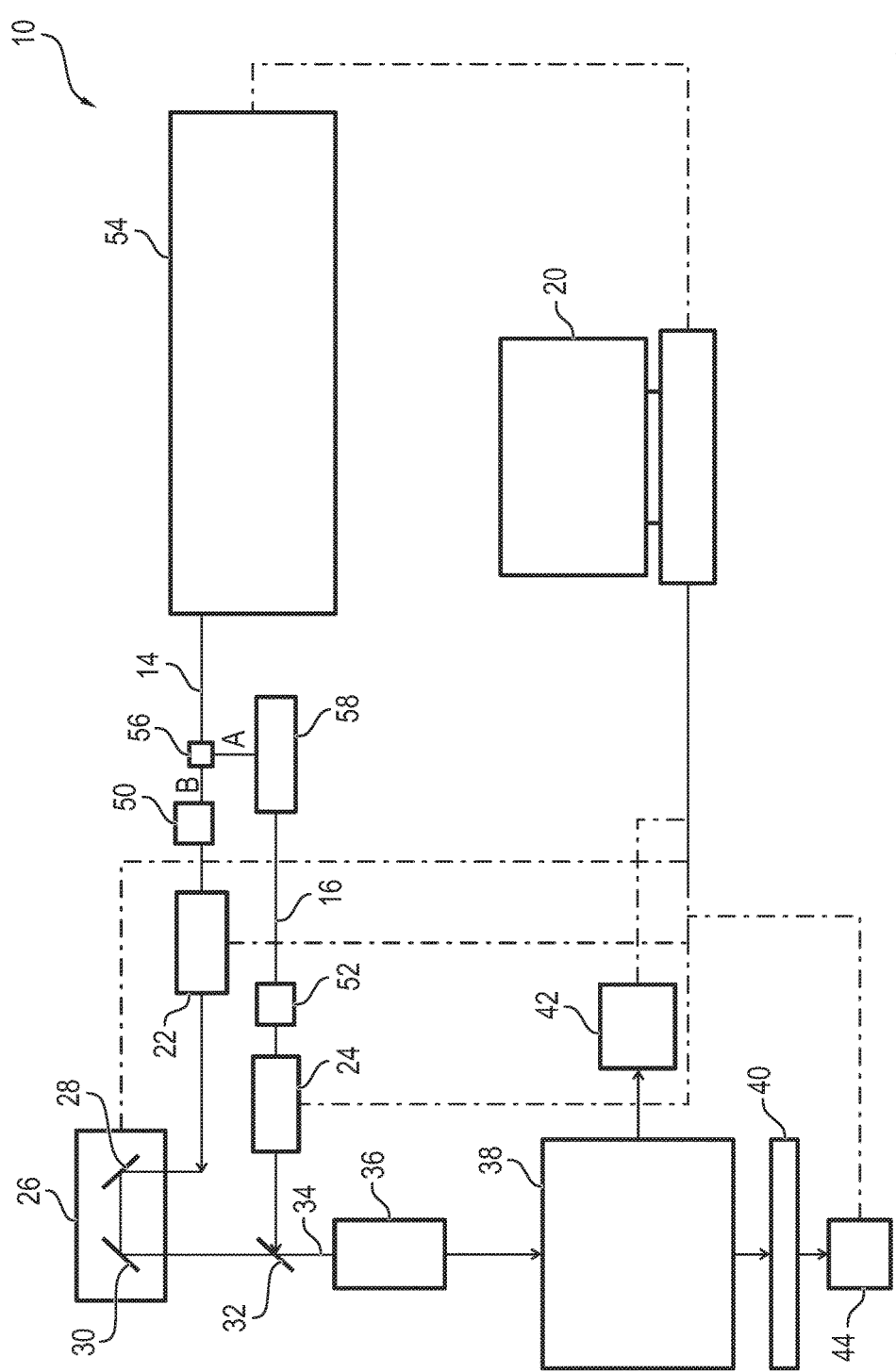
FIG. 9 shows a further modified embodiment of the device according to the present invention.

In the embodiment according to FIG. 9, as in the embodiment depicted in FIG. 7, two controllable chirp units 50, 52 are provided, chirp unit 50 being associated with first light path 14 and chirp unit 52 with second light path 16. In contrast to the embodiment according to FIG. 7, however, in FIG. 9 chirp units 50, 52 are embodied as external units. In addition, what is provided is not two separate femtosecond lasers that are synchronized with one another via a laser synchronization unit, but a single femtosecond laser 54 that comprises a single laser output for outputting the first laser pulse. In this embodiment the second laser pulse is generated by the fact that a beam splitter 56 is arranged in first light path 14 and leads to an optical parametric oscillator (OPO) or amplifier (OPA) 58 that is pulsed by the laser light emitted from femtosecond laser 12. The optical parametric oscillator or amplifier 58 then outputs the second laser pulse along second light path 16.

It is self-evident that the embodiments depicted in FIGS. 4 to 9 are to be understood merely as examples. In particular, the modifications provided in these embodiments are alternately combinable with one another in a technically useful manner.

For each of the embodiments explained above it is assumed that a selective focusing, as depicted in sub-Figure (c) of FIG. 3, is brought about by applying control according to the present invention to the chirp unit associated with first light path 14 and, as applicable, also with second light path 16. This spectral focusing is selected so that overall, a positive chirp is produced. The invention is not limited to an overall positive chirp, however, as is clearly evident from what is depicted in FIG. 10.

Figure 10:
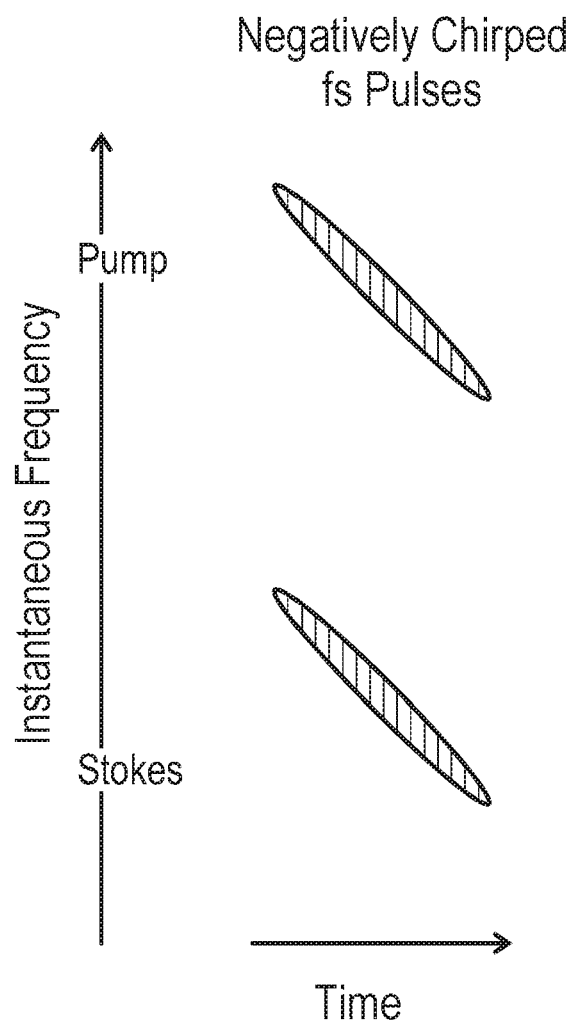
FIG. 10 is a schematic depiction to illustrate impingement of a negative chirp upon the laser pulses.

For what is depicted in FIG. 10 it is assumed that the at least one controllable chirp unit impinges upon the laser pulse or pulses with a negative chirp which is sufficiently large that the positive chirp, introduced e.g. by way of glass block 36 and optionally by further optical system 38, is overcompensated for in such a way that overall, the laser pulses spectrally focused on sample 40 have a negative chirp.

In order to enable particularly user-friendly operation of device 10 according to the present invention, the control parameter with which control system 20 controls the chirp unit associated with first light path 14 or with second light path 16, and the delay parameter with which control system 20 controls delay stage 26, are determined automatically as a function of the wavelength of the first and the second laser pulse. Certain calibration steps are carried out in advance for this purpose, in order to make available corresponding calibration data that are accessed by control system 20 in order to define the control parameter and the delay parameter.

Figure 11:
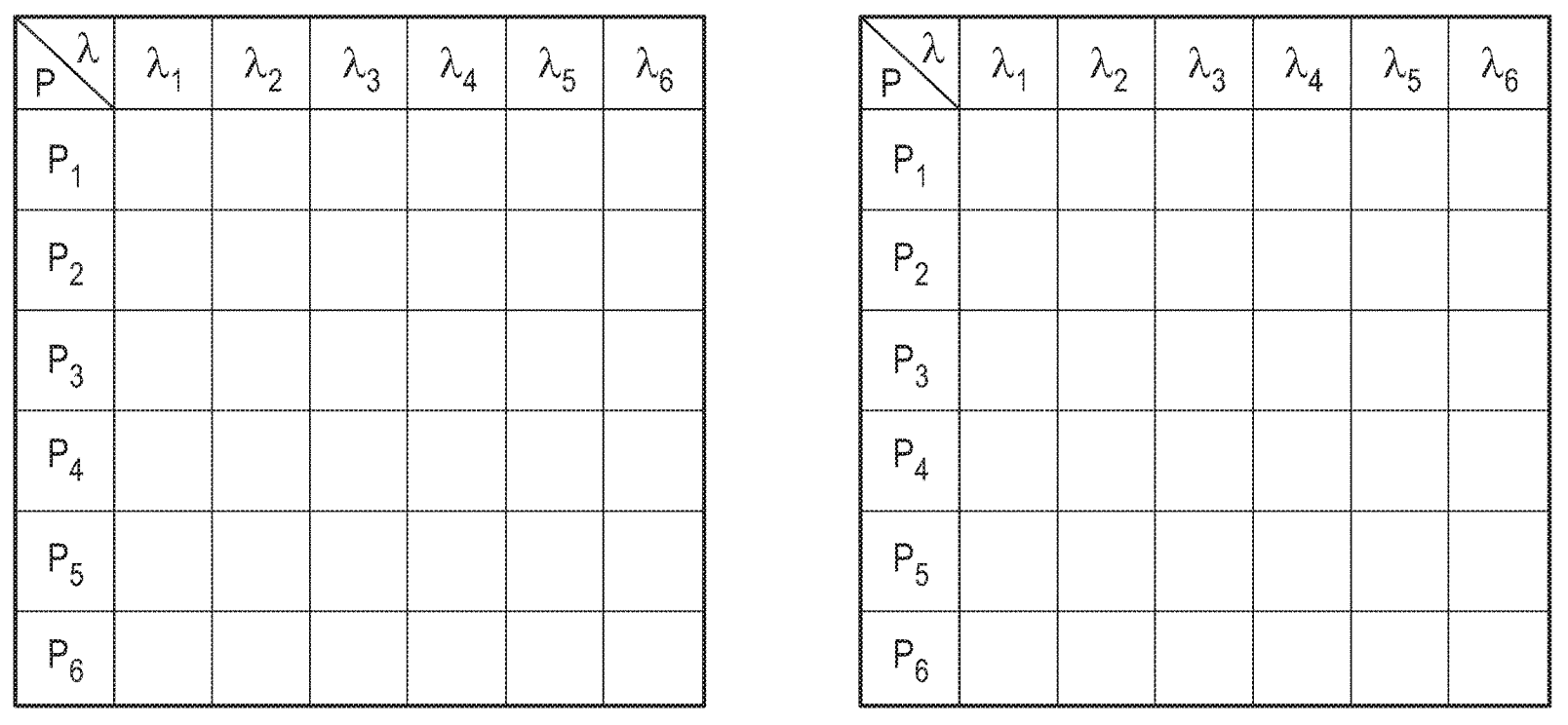

FIG. 11 shows, purely by way of example, the furnishing of such calibration data in the form of calibration tables.

The left table in FIG. 11 represents a matrix in which, for predefined values $\lambda_1$ to $\lambda_6$ of the wavelength of the laser pulse and predefined values $P_1$ to $P_6$ of the control parameter, the respective measured time-related pulse width is to be entered. The pulse width is measured, for example, with the aid of an autocorrelation unit. The respective pulse width is measured twice, namely firstly in the first or second light path 14, 16 immediately after passage through the controllable chirp unit associated with that light path, and secondly in shared light path 34 after passage through optical system 38 or, if the chirp caused by optical system 38 is negligible, after passage through glass block 36 (or through optical element 44 that replaces glass block 36). Based on these two measurements, the chirp introduced at sample 40 can be calculated in simple fashion as a function of the wavelength λ and control parameter P.

Based on the result of the measurements explained above, the control parameter P can be determined, for a predefined value of the variable wavelength λ, in such a way that the desired spectral focusing is achieved.

The right table in FIG. 11 shows a calibration table in the form of a matrix in which, for predefined values $\lambda_1$ to $\lambda_6$ of the variable wavelength λ and for predefined values $P_1$ to $P_6$ of the control parameter P, the values, obtained by a calibration measurement, for the relative delay of the two laser pulses at sample 40 are to be entered. Based on this calibration table, control system 20 can determine in simple fashion the correct delay parameter for a predefined value of the variable wavelength λ.

The calibration data ascertained in the manner explained above are stored, for example, in a calibration file held in control system 20 and are retrieved as necessary in order to ascertain, as a function of the selected wavelength, the correct control parameter for controlling the respective chirp unit and the correct delay parameter for controlling delay stage 26.

What is claimed is:

1. A device for illuminating a sample, having
at least one pulsed laser light source for repeated emission of a first laser pulse along a first light path and of a second laser pulse along a second light path physically separated from the first light path;
a superimposition element for collinear superimposition of the two laser pulses in a shared light path;
a delay stage, arranged in the first or the second light path, for delaying one of the two laser pulses relative to the other laser pulse in such a way that the two laser pulses sent along the shared light path onto the sample exhibit a temporal superimposition;
a shared chirp unit, arranged in the shared light path, for frequency-modifying influencing both of the first laser pulse and of the second laser pulse; and
at least one separate chirp unit, arranged in the first light path, for frequency-modifying influencing only of the first laser pulse,
the shared chirp unit and the separate chirp unit being coordinated with one another in order to achieve a target state in which an instantaneous frequency of the first laser pulse influenced both by the separate chirp unit and by the shared chirp unit, and an instantaneous frequency of the second laser pulse influenced only by the shared chirp unit, have a predefined frequency difference,
wherein at least the wavelength of the first light pulse is variable in a predetermined wavelength range by means of the pulsed laser light source; and
the separate chirp unit is coupled to a control system by which the separate chirp unit is controllable with a control parameter dependent on the wavelength of the first laser pulse in order to establish the target state.

2. The device according to claim 1, wherein in the target state the difference between the instantaneous frequency of the first laser pulse influenced both by the separate chirp unit and by the shared chirp unit, and the instantaneous frequency of the second laser pulse influenced only by the shared chirp unit, is constant during the temporal superimposition of the two laser pulses.

3. The device according to claim 1, wherein the shared chirp unit is constituted by an optical modulator or an optical filter.

4. The device according to claim 1, characterized by an additional separate chirp unit that is controllable for frequency-modifying influencing only of the second laser pulse in the second light path.

5. The device according to claim 1, wherein the at least one separate chirp unit is contained in the pulsed laser light source.

6. The device according to claim 1, wherein the at least one separate chirp unit is arranged outside the pulsed laser light source.

7. The device according to claim 1, characterized by two pulsed laser light sources, of which a first is associated with the first light path and a second with the second light path.

8. The device according to claim 1, wherein one of the two pulsed laser light sources is constituted by an optical parametric oscillator or amplifier that is coupled via a beam splitter to a laser output of the other pulsed laser light source.

9. A method for illuminating a sample, in which method
by means of at least one pulsed laser light source, a first laser pulse is repeatedly emitted along a first light path and a second laser pulse is repeatedly emitted along a second light path physically separated from the first light path;
the two laser pulses are collinearly superimposed in a shared light path;
one of the two laser pulses is delayed relative to the other laser pulse in such a way that the two laser pulses sent along the shared light path onto the sample exhibit a temporal superimposition;
by means of a shared chirp unit arranged in the shared light path, both the first laser pulse and the second laser pulse are influenced in frequency-modifying fashion; and
by means of at least one separate chirp unit arranged in the first light path, only the first laser pulse is influenced in frequency-modifying fashion,
the separate chirp unit and the shared chirp unit being coordinated with one another in order to achieve a target state in which an instantaneous frequency of the first laser pulse influenced both by the separate chirp unit and by the shared chirp unit, and an instantaneous frequency of the second laser pulse influenced only by the shared chirp unit, have a predefined frequency difference,
wherein at least the wavelength of the first light pulse is varied in a predetermined wavelength range by means of the pulsed laser light source; and
the separate chirp unit is controlled by means of a control system with a control parameter dependent on the wavelength of the first laser pulse in order to establish the target state.

10. The method according to claim 9, wherein the first laser pulse and the second laser pulse are respectively approximated by a Gaussian pulse whose normalized electric field E(z,T) is described by the following equation:

$$E(z, T) = \exp\left(-\frac{(1+iC)T^2}{2T_o^2}\right)\exp^{-i(kz-\omega T)},$$

in which z denotes a spatial coordinate in the propagation direction of the respective laser pulse, T denotes time, C denotes a chirp parameter, $T_0$ denotes the pulse duration referred to $e^{-1}$ times the maximum value of the electric field, k denotes the wave number, and ω denotes the frequency, and the control parameter is defined in such a way that the variable $$\frac{C}{T_0^2}$$

is identical for the first laser pulse and the second laser pulse.

11. The method according to claim 9, wherein a calibration is carried out in order to ascertain calibration data on the basis of which the control parameter is determined by means of the control system.

12. The method according to claim 11, wherein in the context of the calibration a chirp parameter is ascertained, as an indicator of the chirp impingement upon the respective laser pulse by the shared chirp unit, both for the first laser pulse and for the second laser pulse.

13. The method according to claim 12, wherein at least the chirp parameter relating to the first laser pulse is determined by measuring the pulse duration of the first laser pulse for predefined values of the control parameter and for predefined values of the wavelength of the first laser pulse, both in the first light path after passing through the separate chirp unit and in the shared light path after passing through the shared chirp unit; ascertaining therefrom a pulse duration difference; and calculating the chirp parameter on the basis of that pulse duration difference.

14. The method according to claim 9, wherein the delay stage is controlled by means of the control system with a delay parameter dependent on the wavelength of the first laser pulse.

15. The method according to claim 14, wherein the delay parameter is ascertained on the basis of further calibration data that are determined by ascertaining the delay of one of the two laser pulses relative to the other laser pulse for predefined values of the control parameter and for predefined values of the wavelength of the first laser pulse.

* * * * *